United States Patent [19]

Wang et al.

[11] Patent Number: 5,496,276

[45] Date of Patent: Mar. 5, 1996

[54] CATHETER BALLOON WITH RETRACTION COATING

[75] Inventors: Lixiao Wang, Minneapolis; Linda J. Vickerman, Anoka, both of Minn.

[73] Assignee: Scimed Life Systems, Inc., Maple Grove, Minn.

[21] Appl. No.: 447,220

[22] Filed: May 22, 1995

Related U.S. Application Data

[62] Division of Ser. No. 124,238, Sep. 20, 1993, abandoned.

[51] Int. Cl.$^6$ ................................................. A61M 29/00
[52] U.S. Cl. ............................. 604/96; 604/99; 604/103; 606/192; 606/194
[58] Field of Search ........................... 604/96, 99, 103; 606/192, 194, 195

[56] References Cited

U.S. PATENT DOCUMENTS

| | | |
|---|---|---|
| 2,690,595 | 10/1954 | Raiche . |
| 3,457,098 | 7/1969 | Leininger et al. . |
| 3,617,344 | 11/1971 | Leininger . |
| 3,846,353 | 11/1974 | Grotta . |
| 4,254,774 | 3/1981 | Boretcs . |
| 4,338,942 | 7/1982 | Fogarty ............................ 606/194 |
| 4,387,833 | 6/1983 | Venus, Jr. . |
| 4,403,612 | 9/1983 | Fogarty ............................ 606/194 |
| 4,413,989 | 11/1983 | Schieldahl et al. . |
| 4,608,984 | 9/1986 | Fogarty ............................ 606/194 |
| 4,637,396 | 1/1987 | Cook ................................ 604/194 |
| 4,646,742 | 3/1987 | Packard et al. . |
| 4,702,252 | 10/1987 | Brooks et al. .................. 604/103 |
| 4,786,556 | 11/1988 | Hu et al. . |
| 4,793,350 | 12/1988 | Mar et al. . |
| 4,884,573 | 12/1989 | Wuay et al. . |
| 4,932,956 | 6/1990 | Reddy et al. . |
| 4,941,877 | 7/1990 | Montano, Jr. . |
| 4,950,239 | 8/1990 | Gahara et al. . |
| 4,994,072 | 2/1991 | Bhate et al. . |
| 5,015,231 | 5/1991 | Keith et al. . |
| 5,026,607 | 6/1991 | Kiezulas . |
| 5,037,392 | 8/1991 | Hillstead . |
| 5,087,246 | 2/1992 | Smith ............................... 604/96 |
| 5,116,318 | 5/1992 | Hillstead ......................... 604/96 |
| 5,147,302 | 8/1992 | Euteneuer et al. . |
| 5,192,296 | 3/1993 | Bhate et al. . |
| 5,195,969 | 3/1993 | Wang et al. . |
| 5,195,970 | 3/1993 | Gahara . |
| 5,226,887 | 7/1993 | Farro et al. ..................... 604/194 |
| 5,272,012 | 12/1993 | Opolski . |
| 5,290,306 | 3/1994 | Trotta et al. ................... 606/194 |
| 5,350,361 | 9/1994 | Tsukashima et al. . |

FOREIGN PATENT DOCUMENTS

| | | |
|---|---|---|
| 420488B1 | 9/1990 | European Pat. Off. . |
| 492361A | 7/1992 | European Pat. Off. . |
| 0553960 | 11/1993 | European Pat. Off. . |
| 2130093 | 5/1984 | United Kingdom . |

OTHER PUBLICATIONS

Product Brochures: "Mitsubishi Shape Memory Polymer", Undated; Processing Instructions For Mitsubshi Shape Memory Polymer, (Apr. 1992); Untitled Exerpt pp. 4–12 and 5 Pages Tables, Undated, Pertaining to Mitsubshi Shape Memory Polymers.

Primary Examiner—C. Fred Rosenbaum
Assistant Examiner—N. Kent Gring
Attorney, Agent, or Firm—Vidas, Arrett, & Steinkraus

[57] ABSTRACT

An inflatable balloon (14) for a catheter (10) includes a coating (15) which causes the balloon to prefer a predetermined, low profile configuration, such as a trifold configuration (40), when deflated. The balloon has a wall (13) which has an exterior polymeric coating (15). The coating (15) is set while the balloon is in the predetermined low-profile deflated configuration so that after inflation, the coating acts to urge the balloon to return to the low profile configuration as the balloon is deflated.

20 Claims, 2 Drawing Sheets

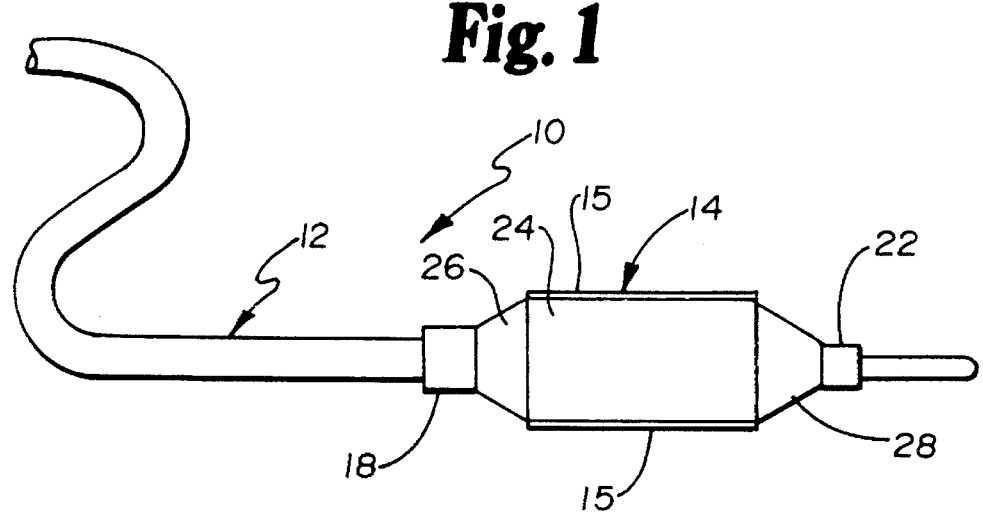
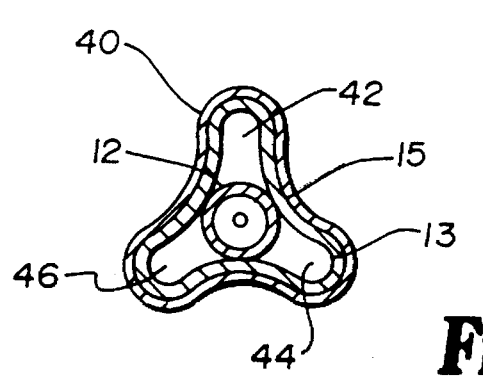
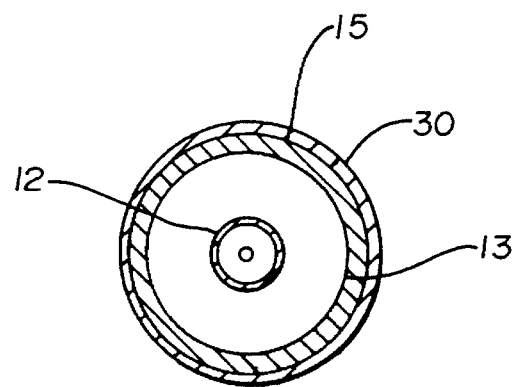
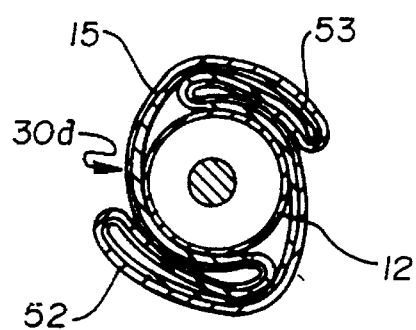

CATHETER BALLOON WITH RETRACTION COATING

This application is a division of Ser. No. 08/124,238 filed Sep. 20, 1993, now abandoned.

BACKGROUND OF THE INVENTION

The present invention relates to a balloon catheter useful in medical dilatation procedures.

Angioplasty has gained wide acceptance in recent years as an efficient and an effective method for treating types of vascular diseases. In particular, angioplasty is widely used for opening stenoses in coronary arteries as well as for treating stenoses in other parts of the vascular system.

The most widely used form of angioplasty makes use of a dilatation catheter which has an inflatable balloon at its distal end. Using fluoroscopy, a physician guides the catheter through the vascular system until the balloon is positioned across the stenoses. The balloon is then inflated by supplying liquid under pressure through an inflation lumen to the balloon. Tile inflation of the balloon causes stretching of a blood vessel and pressing of the lesion into the blood vessel wall to reestablish acceptable blood flow through the blood vessel.

In order to treat very tight stenoses with small openings, there has been a continuing effort to reduce the profile of the catheter so that the catheter can reach and pass through the small opening of the stenoses. There has also been an effort to reduce the profile of the catheter after an initial use and deflation of the balloon to permit passage of the catheter through additional lesions that are to be treated or to allow entry and retreatment of lesions that reclose after initial treatment. It is also desired that the balloon component of the catheter deflate from an inflated mode to a predictable and reduced profile so that the balloon catheter can be withdrawn from a blood vessel without becoming caught.

Reducing a catheter profile requires a consideration of two deflated balloon profiles. The initial profile is that of the unused catheter before it is inserted into a blood vessel for the first time. This profile may be controlled by the wrap given to the deflated balloon by the manufacturer or the surgeon. The second deflated balloon profile is that obtained after the catheter has been used and the catheter balloon has been inflated and deflated within the body. The second profile is rarely, if ever, as compact as the first deflated profile and, with many balloon materials often takes an entirely different appearance.

One factor manipulated to reduce the profile of the dilatation catheter is the wall thickness of the balloon material. Balloons for dilatation balloon catheters have been made from a wide variety of polymeric materials. Typically the balloon wall thicknesses have been on the order of 0.0004 to 0.003 inches for most materials. There have been continuing efforts, however, to develop ever thinner walled balloon materials, while still retaining the necessary distensibility and burst pressure rating, so as to permit lower deflated profiles.

Another factor manipulated to reduce the profile of the catheter is the conformation of the balloon which is altered so that the balloon acquires a low profile shape when the balloon is deflated. Typically, oriented PET balloons (a very common catheter balloon material) forms a pair of opposed radially extending flat wings when subjected to a negative pressure. This winged configuration can easily be wrapped to give a low profile which facilitates insertion of the balloon of the catheter through a blood vessel constriction, however, rewrapping is not easily accomplished after inflation in the body so that the second deflated balloon profile is usually less compact. The wings typically extend diametrically at a distance substantially larger than the diameter of the catheter. The wings may then interfere with a smooth withdrawal of the catheter and even become caught in blood vessels. The force required for a catheter with its balloon in its second deflated profile to recross a treated lesion is therefore typically greater than the force required to initially cross the lesion with the balloon in its initial wrapped profile.

Other problems exist with common balloon materials. For instance, oriented PET balloons formed by stretch blow molding can exhibit pin holes that emit a high-velocity jet of inflation fluid during inflation. This jet may cause artery dissection. PET also exhibits low tear resistance. Because of their thin walls, the balloons are very susceptible to damage, and must be handled with extreme care. PET also will not take a crease, which would be advantageous to facilitate wrapping the balloon.

Smith, U.S. Pat. No. 5,087,246, issued Feb. 11, 1992, describes a balloon dilatation catheter with a fluted balloon having three wings. The balloon in the Smith patent requires that a wire attached to a metal band near the proximal end of the balloon and secured to the balloon at the distal end of the balloon impart a tension to the balloon that will insure that the balloon will assume the fluted configuration when deflated.

It has also been reported in U.S. Pat. No. 4,403,612 4,338,942 and 4,608,984, that the problem of rewrapping inelastic catheter balloons can be addressed with dual balloon constructions in which an outer, smaller, balloon of a highly elastic material such as latex, encloses the inelastic dilatating balloon element. On deflation the elastic balloon is used to compress the dilatation balloon.

A different type of double balloon construction is employed in copending application 07/927,062, filed Aug. 6, 1992 to provide a dilatation element with non-linear compliance characteristics.

A dilatation balloon is disclosed in EP 420,488 which employs two different concentrically co-extruded polymers to produce a dual layer balloon. An optional lubricity enhancing hydrophilic coating is also mentioned.

It is also known to apply a silicone fluid to the exterior of a dilatation balloon to increase lubricity.

There remains a need in the art to provide improved methods of reducing the profile of deflated dilatation balloons after use, especially non-compliant balloons of inelastic materials such as oriented PET.

SUMMARY OF THE INVENTION

The present invention in one aspect is a balloon for a dilatation catheter comprising a balloon wall, the wall having an exterior polymeric coating, the coating being set to prefer a predetermined low-profile deflated configuration of the balloon, such as a trifold configuration. Catheters having dilatation elements comprising a balloon of the invention are also included in the invention.

The invention also includes a method for treating an inflatable balloon to prefer a predetermined, low profile deflated configuration so that, after inflation to a dilatation pressure, the balloon reattains the predetermined deflated configuration when the balloon is deflated. The method includes forming the balloon into a predetermined low profile deflated configuration, coating the balloon with a polymeric coating formulation and then setting the coating while the balloon is maintained in the low profile deflated configuration.

BRIEF DESCRIPTION OF THE DRAWINGS

FIG. 1 is a perspective view of a dilatation catheter that includes an inflated coated balloon of the present invention.

FIG. 2 is a cross sectional view of the balloon portion of a catheter as in FIG. 1.

FIG. 3 is a cross sectional view as in FIG. 2 of one embodiment of the invention with the balloon in a partially deflated configuration.

FIG. 5 is a cross-sectional view of a balloon of the invention in an alternate S-fold deflated configuration.

DETAILED DESCRIPTION OF THE PREFERRED EMBODIMENTS

Figure 4:
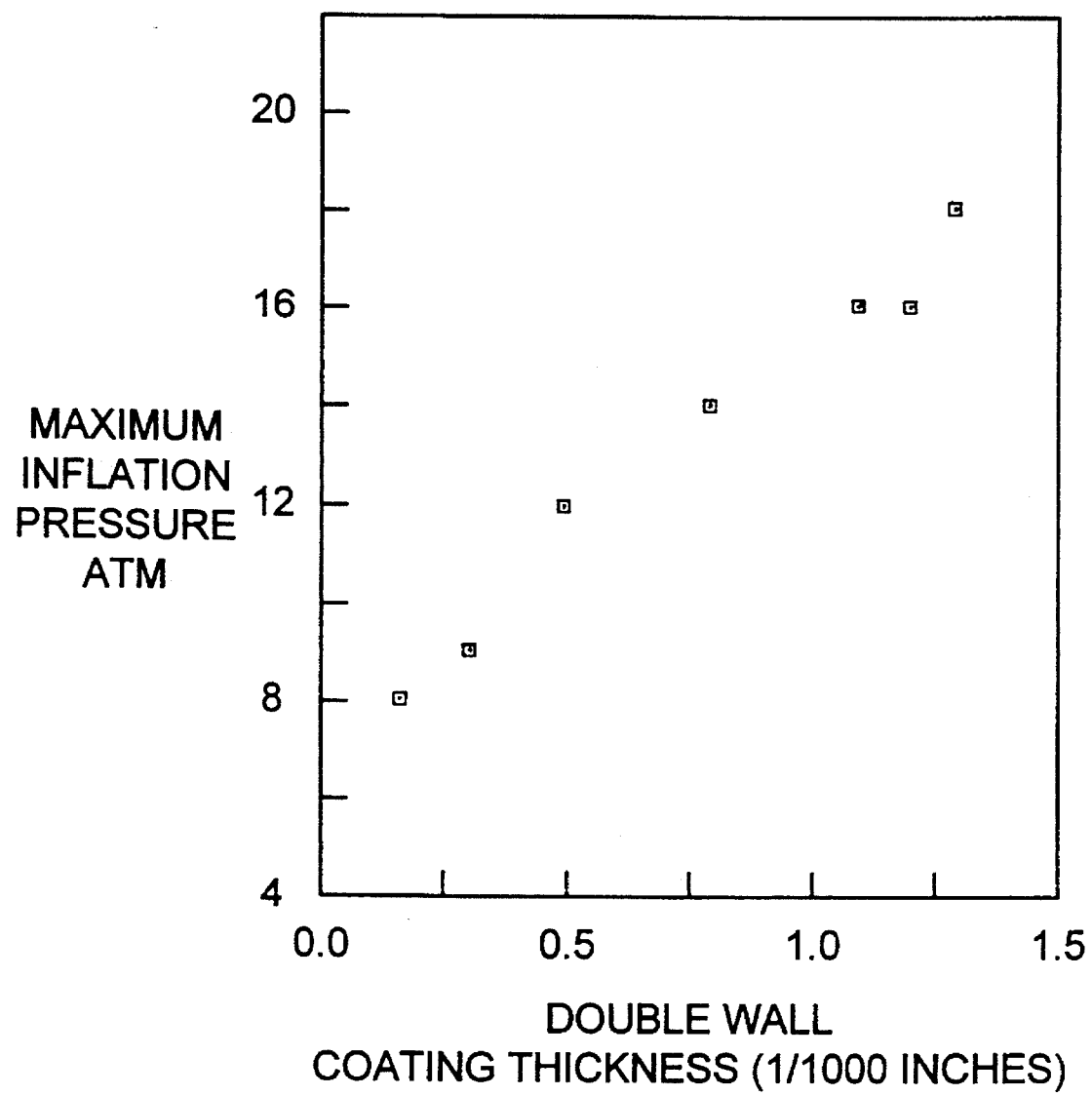
FIG. 4 is a graphical view of the maximum pressure applicable to inflate an uncoated control balloon and several coated balloons of the invention having varying coating thicknesses, and still have the balloons reattain their preset configuration when deflated.

A dilatation balloon catheter of the present invention, illustrated generally at 10 in FIG. 1, includes an inflatable balloon 14 mounted at the distal end of an elongated flexible shaft 12. Except an noted herein, catheter 10 is conventional in its construction, providing a lumen communicating with the interior of balloon 14, for inflation and deflation of the balloon, and other optional features conventional in the dilatation catheter art. The balloon 14 has an inflated configuration, illustrated in FIGS. 1 and 2, and a preshaped, low profile, deflated configuration, illustrated for one trifolded balloon embodiment at 40 in FIG. 3.

The balloon comprises balloon wall 13 formed of a material, such as biaxially oriented PET, which provides the balloon with its essential compliance characteristics. The balloon wall 13 may be noncompliant and made of stiff materials such as PET, high density polyethylene, polyamides, polycarbonates and stiff polyurethanes. The balloon wall 13 may also be compliant, made of materials such as polyvinyl chloride, polyethylene, polyester copolymers, polyolefin copolymers and the like. The invention provides particular advantage when the balloon wall 13 is made of a noncompliant material such as oriented PET.

Suitable balloon forming techniques which may be employed to form the balloon wall are well known and are described, for instance, in U.S. Pat. No. 4,490,421 to Levy. A particularly preferred balloon wall material is a 0.64–0.8 IV PET polymer which may be formed into a balloon as described in copending application Ser. No. 07/963,678, filed Sep. 29, 1993, incorporated herein by reference. Advantageously, extruded PET tubes used to form the balloons are desiccated prior to stretching and blowing the tubes to form the balloon. Other techniques for forming dilatation balloons may also be employed to form the balloon wall 13.

Balloon 14 has a coating 15 over balloon wall 13. The coating polymer is desirably sufficiently flexible and elastic at body temperature that the coating has only a minor, if any, impact on the compliance characteristics of balloon 14. Suitable polymers include elastomeric copolymers, graft and block polymers, and blends of these polymers. The polymers may be thermoplastic or thermoset polymeric materials. Desirably, the coating is of a polymer which, at the thickness employed and at body temperature (37° C.), displays greater shape memory than the balloon wall 13. However it is not essential that the coating polymer have particularly good shape memory properties. The most preferred polymeric materials include flexible hydrophobic or hydrophilic polyurethane which are designed especially for their shape memory properties. Such shape memory polymers are described, for instance, in "Processing Instructions For Mitsubishi Shape Memory Polymers," Manual #1, Rev. 2.2, April 1992, Mitsubishi Heavy Industrials, Ltd.; U.S. Pat. No. 4,950,258 (homopolymers of lactide and glycolide and lactide/glycolide copolymers); JP (1984) 53528 (norbornene polymers); U.S. Pat. No. 4,820,298 (polyester/polycarbonates); and U.S. Pat. No. 5,163,952 (polymethacrylate copolymers). Other suitable coating polymers include polyesters, polycarbonates, polyamides, polyolefins and polyacrylates. Shape memory polymers having a Tg between 23° C. and 37° C. are particularly preferred. An example of a preferred polyurethane coating polymer is MM 2510™, manufactured by Mitsubishi Heavy Industrials, Ltd. of Japan (Tg 25° C.).

It is believed that polymers having a glass transition temperature that is less than 37 degrees Centigrade will provide especially beneficial properties of additional softness and flexibility which further contributes to the trackability of the catheter as it is transported through a blood vessel.

The coating 15 is employed at a thickness which is effective to increase, as compared to an uncoated balloon of the same size and material, the inflation pressure that the balloon 14 can sustain and still reattain a preshaped deflated configuration. Preferably, the coating is sufficient to permit the balloon to be inflated to a pressure to at least 9 atm, more preferably to a pressure within the range of 13 to 18 atm, and still return to the preshaped configuration upon deflation. In some cases it may be desirable to employ a coating having a greater thickness than the balloon wall 13. However, as such thick coatings can contribute substantially to the initial and second deflated profiles of balloon, it will generally desired that the coating be employed at a minimum thickness effective to effect refolding of the balloon to the preshaped configuration upon deflation after inflation at a typical maximum use pressure for the balloon. Effective coating thicknesses will typically fall in the range of 0.0001–0.0015 inches, preferably 0.0005–0.0010 inches (double wall basis).

The coating is set at a predetermined deflated configuration so that it acts to return the balloon to that configuration upon deflation. The coating may be set by applying a solution of the coating polymer in a suitable solvent to the exterior of balloon wall 13 after the balloon has been formed into the desired deflated configuration and then evaporating the solvent while the balloon remains in that deflated configuration. If the coating polymer will take a physical heat set, elevated temperature may be employed to set the polymer, provided that the physical properties of the underlying balloon wall material are not affected. For curable materials the applied coating should be cured in the desired deflated configuration. Depending on the particular technique employed to form the balloon into the predetermined deflated configuration it may also be possible, with some coating formulations, to reorder the sequence of steps so as to apply the formulation to the inflated balloon, form the balloon into the predetermined deflated configuration and then complete drying or curing of the coating material. Application may be accomplished by dip coating, spraying or any other suitable technique.

A preferred predetermined deflated configuration is a trifold configuration as illustrated in FIG. 3, in partially deflated condition (deflation is accomplished under negative pressure so that the opposing walls of the balloon contact each other in fully deflated condition). The trifolded balloon includes three lobes, 42, 44 and 46 which disappear on full inflation but reform upon deflation of the balloon. The three lobe configuration has been found to easily wrap about the catheter 10. The trifold may be made by placing a catheter having an uncoated balloon installed on its distal end in a trifold fixture with the balloon inflated, typically at 1–3 atmospheres pressure. The fixture contains three blades spaced radially at 120° separation about the axis of the balloon. The blades are brought into contact with the balloon and advanced radially inward as the balloon is deflated. When fully deflated, the blades are retracted and the catheter removed from the fixture. The balloon is then coated, for instance by dipping in a suitable polymer solution.

Other low profile configurations, such as an S-fold configuration are suitable for employment as the predetermined deflated configuration in the present invention. In FIG. 5 there is shown an S-folded balloon 30a which has an alternate deflated configuration including two bent lobes 52 53 so that the deflated configuration resembles the letter S. The S-folded deflated configuration has also been found to easily wrap about a catheter shaft. Multi-lobe configurations, for instance where the number of lobes is 4 or 5, can also be employed. Those skilled in the art can readily adapt the techniques disclosed herein for forming such alternate predetermined configurations.

The coating 15 is most preferably prepared from a solution of the coating polymer in an acceptable solvent. The solvent must be able to dissolve the polymer without dissolving the balloon wall material. The solvent also must not affect physical properties of the balloon such as burst pressure, burst modes, compliance, the profile of the wrapped balloon, the stiffness of the balloon and tractability of the catheter with the coated balloon. Acceptable solvents will therefore vary depending on the balloon wall material. Suitable solvents for coatings on PET balloons include acetone, methyl acetate, ethyl acetate, dioxane, alcohols, chloroform, methylene chloride, acetonitrile, toluene, methyl ethyl ketone, tetrahydrofuran, dimethylformamide, dimethylsulfoxide and mixtures of these solvents. The polymer may usually be dissolved in the solvent by shaking or by stirring at room temperature. If necessary, an elevated temperature may be employed to form the polymer solution.

The coating thickness on the balloon may be adjusted by the concentration of the polymer solution and, the number of times the balloon is dipped in the solution or the time and density of spray. The concentration of polymer in the solution depends upon the type of solvent, the polymer, the balloon material and the coating thickness desired. Typically, the concentration of polymer in the solution is in a range of about 1 to 50% by weight.

Regardless of application method, coverage of the coating can be limited to balloon 14, or just parts of balloon 14, by covering portions of the catheter and balloon which are not to be coated during application of the coating formulation. In particular, the coating will typically be selectively excluded from the catheter tip 16 and balloon waist portions 18, 22 in this manner. In some cases it may be advantageous to exclude the cone portions 26, 28, so that the coating is limited to central body portion 24 of the balloon.

To assure that the balloon retains its predetermined deflated configuration until the coating has set it is preferred that negative pressure applied during the forming step be maintained until the coating has fully dried or cured. Ambient temperature will usually suffice for drying or curing the coating, but elevated temperatures may be employed to speed the process if desired or if needed to fully evaporate the particular solvent selected or fully cure the coating material. For solvent coatings the time for drying may range from about 0.1 to 36 hours or even longer. Once the coating has set the catheter 10 is wrapped, packed and sterilized.

The set coating provides balloon with a memory of the deflated conformation. As a consequence, the balloon will return to the deflated configuration at which the coating was set after being inflated, even after multiple inflations and inflation to pressures much greater than pressures at which an uncoated balloon of the same material and size can return the deflated configuration. By way of illustration, when typical uncoated oriented PET balloons are formed to a trifolded deflated configuration, the maximum inflation pressure achievable before the uncoated balloon will lose its capacity to return to the initial trifolded shape upon deflation will range from about 2 to 8 atm. The same types of balloons, when folded and then coated according to the present invention, will achieve maximum inflation pressures of from about 9 atm to about 17 atm, depending upon the thickness of the balloon coating and the thickness of the balloon wall, before losing their ability to return to the initial trifold configuration when deflated.

Additionally, preferred embodiments of the invention provide a further improvement over uncoated catheter balloons because the balloon 14 is coated with a material that has a soft and pliable. Because the coating is soft and pliable to the touch, the balloon has a reduced tendency to become snagged on a protrusion in a blood vessel, to become caught in a stenosis or to scratch or traumatize a blood vessel during transport of the catheter within the blood vessel.

Balloon 14 may optionally also include a lubricity enhancing coating (not shown), applied over coating 15. Silicone fluids and other materials used in the art for this purpose may be employed in conventional amounts.

Specific examples of the coated catheter balloon of the present invention are presented below. The examples presented are not intended to limit the balloon 14 having the coating 15 of the present invention.

EXAMPLE 1

A polyurethane polymer, designated Pellethane™ 2103–70A, manufactured by Dow Chemical of Midland, Mich., was dissolved in a tetrahydrofuran solvent at room temperature to form five polymer coating solutions. The solutions included polymer concentrations of 2.5, 5.0, 7.5, 10 and 12 percent by weight.

The balloon catheter coated with one of the five solutions was of a dual lumen design having a 3.0 mm balloon bonded onto the catheter. The balloon was made of a biaxially oriented polyethylene terephthalate material and was trifolded.

The catheter having the balloon bonded to the shaft was immersed in one of the polymer solutions for 2 seconds. The catheter was then dried at room temperature for at least 2 hours. Next, the catheter was coated with a conventional lubricating silicone solution. The coated catheter was then sterilized under ethylene oxide by conventional methods.

The balloon double wall thickness for each catheter was about 0.0011 inches (0.00055 inches single wall thickness). The double wall coating thicknesses of the coated balloons ranged from 0.00015, 0.00030, 0.00050, 0.00080, 0.0011, 0.0012, and 0.0013 inches. Catheters with uncoated balloons (coating thickness 0.0 inches) were used as controls. At each thickness 2–5 balloons were tested. The balloons were inflated and deflated at progressively increasing inflation pressures until they no longer returned to the trifold configuration upon deflation. The measurements of maximum inflation pressure were performed in a water bath having a temperature of about 37 degrees Centigrade. The pressure increment was 1 atm. The time of each inflation was 1 minute. The reattainment of the trifolded configuration was checked visually. The highest pressure attained with retraction to the trifold configuration was recorded. The average result for each thickness is shown in FIG. 4.

The trifolded coated balloons retained their trifolded configuration when inflated up to pressures of 8, 9, 12, 14, 16, and 18 atm, for the respective 0.00015, 0.00030, 0.00050, 0.00080, 0.0011, 0.0012, and 0.0013 inch coating thicknesses. Except for the thinnest coating these performances were all better than the performance of an uncoated control (8 atm).

EXAMPLE 2

The catheter, coating method and testing method were the same as described in Example 1. The polymer used in the coating was MM 2510™, manufactured by Mitsubishi of Japan. The polymer concentration was about 18% by weight. The solvent was dimethylformamide (DMF). Ten dual lumen catheters with 3.0 mm balloons were coated. The average single wall coating thickness was about 0.00045 inches. The balloon single wall thickness was 0.00055 inches. The average maximum inflation pressure at which the balloons reattained a trifolding pressure was 16 atm. This compares with 8 atm pressure for the dual lumen catheter without the coating.

Both of the polyurethane polymers, Pellethane™ 2103–70 and MM 2510™, when applied to a balloon, performed substantially better than the uncoated balloon. It is believed that the MM 2510™ polyurethane coating performed better than the Pellethane™ 2103–70A polyurethane coating because the Peltethane™ 2103–70A had a glass transition temperature that was much less than room temperature while the Mitsubishi polyurethane polymer had a higher glass transition temperature. Additionally, the Mitsubishi polyurethane polymer is believed to have a better shape memory than the Dow polyurethane polymer.

EXAMPLE 3

The catheters, coating method and testing methods were the same as described in Example 1. However, a smaller balloon size of 2.75 mm was used. The balloons had a thickness of 0.0005 inches with an average coating thickness of 0.0004 inches (single wall basis). The maximum inflation pressure sustained with retraction to the trifold configuration for a coated balloon was 18 atm. This inflation pressure was much greater than observed for an uncoated balloon control.

EXAMPLE 4

The coating method and testing methods were the same as described in Example 1. However, a different catheter design was employed. The catheters used were coaxial catheters, NC-Shadow™ catheters, manufactured by SciMed Life Systems of Maple Grove, MN, with a 3.00 mm balloon. The balloon single wall thickness was 0.00055 inches.

In a control run, 10 coaxial catheters were trifolded but not coated. The average maximum inflation pressure sustained by these catheters having uncoated balloons and a trifolded deflation configuration was 2.4 atm. Above 2.4 atm, the balloons did not retract to the trifolded configuration when deflated.

In accordance with the invention balloons having a trifolded deflation configuration were coated with a 7% Pellethane™ 2103–70A polyurethane tetrahydrofuran polymer solution. The average inflation pressure sustained with retraction to the trifold on deflation was 6.7 atm.

In another embodiment of the invention, eight balloons having a trifolded deflation configuration were coated with a polymer solution having an 18% MM 2510™ shape memory polymer in dimethylformamide. The average inflation pressure sustained with retraction to the trifold was 12 atm.

EXAMPLE 5

The coating method, testing method and catheters were the same as described for Example 4. The only variable changed was the thickness of the balloons tested. The thickness was reduced by about 30 percent to 0.00045 inches. Five balloons having the reduced thickness were tested. The balloons were coated with the polyurethane MM 2510™ shape polymer to a thickness of about 0.00045 inches and were preshaped to a trifolded deflated configuration. The maximum inflation pressure sustained by the coated balloons ranged from 19 to 20 atm before the balloons could no longer reattain the trifold configuration when the balloon was deflated. The inflation pressure of 19 to 20 atm approached the burst pressure of the balloons.

EXAMPLE 6

Biaxially oriented PET balloons having body wall thickness of 0.00045 inches (single wall thickness), a 20 mm length, a 3.0 mm inflated diameter and a 15° cone angle were mounted and trifolded on catheter bodies of the type employed in commercial NC Shadow™ catheters sold by SciMed Life Systems. Catheters with uncoated balloons were compared to catheters having 0.0004 inch thick (single wall basis) coatings of MM 2510™ shape memory polymer. Conventional silicone lubricant was applied to all catheters. Standard tests were employed to determine the force required to be applied to the catheter for the balloon to recross a lesion after being inflated to 12 atm for 1 min. The recrossing force of the catheters without the coating of the invention was 0.16 lb whereas the force required for the catheters coated in accordance with the invention was only 0.10 lb.

In similar experiments using similar balloons, except that they had 45° cone angles, mounted on SciMed Life Systems NC Cobra™ type catheter bodies, the recrossing force of the catheters without the retraction coating of the invention was 0.28 lb whereas the force required for those with the retraction coating was 0.22 lb.

Although the present invention has been described with reference to preferred embodiments, workers skilled in the art will recognize that changes may be made in form and detail without departing from the spirit and scope of the invention.

What is claimed is:

1. A method for treating a dilatation balloon to prefer a preshaped, deflated folded configuration so that, after inflation to a dilatation pressure, the balloon reattains the preshaped deflated folded configuration when the balloon is deflated, the balloon being made of a wall material, the method comprising forming the balloon into said preshaped deflated folded configuration, coating the balloon with a formulation comprising a coating polymer before or after said forming step and, while the balloon is in said preshaped deflated folded configuration, setting the coating, the coating material and thickness being selected to provide the balloon with the property that the balloon will return to the preshaped folded configuration upon deflation after inflation to a pressure at least one atmosphere higher than the pressure which the same balloon preshaped in the same configuration, but uncoated, would withstand and return to its preshaped folded configuration.

2. The method of claim 1 wherein the coating formulation is applied as a solution of the coating polymer in a solvent, inert to the balloon wall material, and is set by drying the applied solution while the balloon is maintained in said preshaped folded deflated configuration.

3. The method of claim 2 wherein the coating is applied by dipping the balloon into the coating polymer solution.

4. The method of claim 2 wherein the coating is applied by spraying the coating polymer solution onto the balloon.

5. The method of claim 1 wherein the coating formulation is a thermoset formulation and is set by curing the formulation while the balloon is maintained in said preshaped folded deflated configuration.

6. The method of claim 1 wherein the coating polymer is a polymer having greater shape memory than the balloon wall material.

7. The method of claim 1 wherein the coating polymer is a shape memory polymer.

8. The method of claim 7 wherein the coating polymer is a polyurethane.

9. The method of claim 1 wherein the coating material and thickness are selected to provide the balloon with the property that the balloon will return to the predetermined low profile configuration upon deflation after inflation to a pressure of at least 9 atm.

10. A method as in claim 9 wherein said inflation pressure is at least 13 atmospheres.

11. The method of claim 1 wherein the balloon wall material is selected from the group consisting of polyethylene terephthalate, high density polyethylene, polyamides, polycarbonates and stiff polyurethanes, polyvinyl chloride, polyethylene, polyester copolymers and polyolefin copolymers.

12. The method of claim 11 wherein the balloon wall material comprises polyethylene terephthalate.

13. The method of claim 1 wherein the coating is applied to a thickness, double wall basis, within the range of 0.0001 to 0.0015 inches.

14. The method of claim 13 wherein the coating applied to a double wall coating thickness of 0.0005 to 0.0010 inches.

15. The method of claim 1 wherein the coating polymer has a glass transition temperature less than 37 degrees Centigrade.

16. The method of claim 1 wherein the coating material is applied as a curable formulation and is set by curing the formulation on the balloon while the balloon is maintained in said preshaped deflated folded configuration.

17. The method of claim 1 wherein the preshaped deflated folded configuration is a trifolded configuration.

18. The method of claim 1 wherein the preshaped deflated folded configuration is an S-folded configuration.

19. The method of claim 1 wherein the coating polymer is a polymer which displays greater shape memory at body temperature than the material of the balloon wall.

20. The method of claim 1 wherein the coating polymer is an elastomer.

* * * * *

UNITED STATES PATENT AND TRADEMARK OFFICE
CERTIFICATE OF CORRECTION

PATENT NO. : 5,496,276

DATED : March 5, 1996

INVENTOR(S) : LIXIAO WANG-ET AL

It is certified that error appears in the above-identified patent and that said Letters Patent is hereby corrected as shown below:

Col. 1, line 22, delete "Tile" and insert -- The --

Signed and Sealed this

Eighteenth Day of June, 1996

Attest:

BRUCE LEHMAN

*Attesting Officer*     *Commissioner of Patents and Trademarks*